United States Patent [19]

Rodriguez et al.

[11] 4,145,343
[45] Mar. 20, 1979

[54] 6'-AMINO-SPIRO[CYCLOALKANE-1,2'-PENAM]-3'-CARBOXYLIC ACID DERIVATIVES

[75] Inventors: Ludovic Rodriguez, Brussels; Jacques Leclercq, Braine l'Alleud, both of Belgium

[73] Assignee: UCB Societe Anonyme, Saint-Gilles-lez-Bruxelles, Belgium

[21] Appl. No.: 800,083

[22] Filed: May 24, 1977

[30] Foreign Application Priority Data

May 25, 1976 [GB] United Kingdom ............... 21624/76

[51] Int. Cl.² .......................................... C07D 499/44
[52] U.S. Cl. ................................ 260/239.1; 424/271; 260/306.7 C
[58] Field of Search ............... 260/239.1 TB, 306.7 C; 424/270, 271

[56] References Cited

U.S. PATENT DOCUMENTS 2,985,648   5/1961   Doyle et al. ................. 260/239.1
3,904,607   9/1975   Kamiya et al. ............. 260/306.7 C
3,957,764   5/1976   Lund ............................ 260/306.7

Primary Examiner—Nicholas S. Rizzo
Attorney, Agent, or Firm—Wenderoth, Lind & Ponack

[57] ABSTRACT

6'-Amino-spiro[cycloalkane-1,2'-penam]-3'-carboxylic acid derivatives having the formula

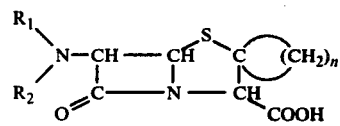

wherein n is a whole number of from 3 to 6 and $R_1$ and $R_2$ represent substituents known in the chemistry of penicillins, and their pharmaceutically acceptable, non-toxic salts, have valuable antibacterial properties and are useful as therapeutic agents in the treatment of infectious diseases caused by Gram-positive and Gram-negative bacteria. Processes for preparing these compounds are also described.

15 Claims, No Drawings

6'-AMINO-SPIRO[CYCLOALKANE-1,2'-PENAM]-3'-CARBOXYLIC ACID DERIVATIVES

The present invention relates to new anti-bacterially-active 6'-amino-spiro[cycloalkane-1,2'-penam]-3'-carboxylic acid derivatives and to processes for preparing the same.

The penicillins, which constitute an important family of antibiotics, have been and continue to be the subject of considerable research. Generally speaking, the penicillins are a family of compounds which correspond to the following general formula:

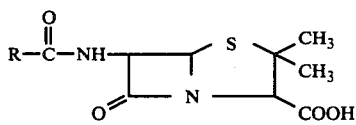

in which R may represent one of a multitude of substituents, those most currently used being mentioned, for example, in Ullmann's Encyklopadie der Technischen Chemie, 4th edition, vol.7,(1974),p.651–652.

Most of the investigations hitherto carried out in this field were based on the search for new substituents R, while the basic ring system of the molecule remained unchanged. Nevertheless, some attempts have been made to study the influence of some variations in the ring system on the activity of the compounds thus obtained. Thus, compounds have been proposed which are similar to the penicillins but in which the gem-dimethyl group situated in the alpha-position with regard to the sulfur atom was replaced by other groups. The following groups have been proposed:

(Belgian Patent Specification No. 738,131)

and

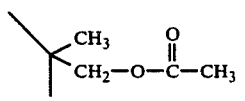
(D.H.R. Barton et al., Chem.Commun.13, (1970), 1683–1684)

However, it was concluded at the time of these different attempts that the nature of these substituents on the carbon atom in the alpha-position with regard to the sulfur atom was not essential to the antibacterial activity of the penicillins (in this regard see, for example, R. J. Stoodley, Progress in Organic Chemistry,8,(1973), 106). More recently, the following groups have also been proposed:

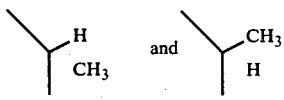
(P.J. Claes et al., Eur.J.Med. Chem.—Chimica Therapeutica, 10, (1975), 573–577)

The conclusion reached with regard to antibacterial activity was the same.

The work which we have done in this field shows that it is possible, by appropriate substitution of the carbon atom in the alpha-position with regard to the sulfur atom, to obtain compounds which have valuable antibacterial properties at least equal and sometimes superior to those of the corresponding penicillins. These new compounds and the preparation thereof form the subject matter of the present invention.

The nomenclature used hereinafter is that proposed by R. J. Stoodley, loc.cit., 102—103. In particular, the name "penam" is given to the following ring system:

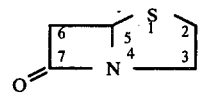

Therefore, it is an objet of the present invention to provide new antibacterial agents and more particularly 6'-amino-spiro[cycloalkane-1,2'-penam]-3'-carboxylic acids carrying in the 6'-position a substituent selected from the substituents known from the chemistry of penicillins, such as those mentioned, for example, in Ullmann's Encyklopädie der Technischen Chemic, (loc.cit.).

More particularly, the present invention relates to 6'-amino-spiro[cycloalkane-1,2'-penam]-3'-carboxylic acid derivatives of the general formula:

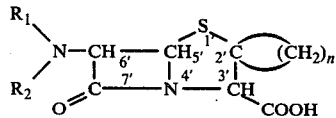

wherein n is a whole number of from 3 to 6, $R_1$ is a hydrogen atom and $R_2$ is one of the radicals known in the chemistry of the penicillins and preferably a 2-phenylacetyl, 2,6-dimethoxybenzoyl, 2-amino-2-phenylacetyl, 5-methyl-3-phenyl-4-isoxazolecarbonyl or 2-carboxy-2-phenylacetyl radical, or $R_1$ and $R_2$ together represent a bivalent radical $R_3$, preferably the (hexahydro-1H-azepin-1-yl)-methylene radical; and the pharmaceutically acceptable, non-toxic salts thereof, preferably the sodium and potassium salts.

The compounds of the present invention are, therefore, compounds having a structure similar to that of the penicillins, but in which the carbon atom in the alpha-position with regard to the sulfur atom is substituted by an alkylene chain which forms a cycloalkyl group with this carbon atom.

Thus, when the substituent $R_2$ is a 2-phenylacetyl radical, the compounds of the present invention are similar to benzylpenicillin (penicillin G); when the substituent $R_2$ is a 2,6-dimethoxybenzoyl radical, the compounds of the present invention are similar to methicillin; when $R_2$ is a 2-amino-2-phenylacetyl radical, the compounds of the present invention are similar to ampicillin; when the radical $R_2$ is a 5-methyl-3-phenyl-4-isoxazolecarbonyl radical, the compounds of the present invention are similar to oxacillin; and, finally, when the radical $R_2$ is a 2-carboxy-2-phenylacetyl radical, the compounds of the present invention are similar to carbenicillin.

When $R_1$ and $R_2$ together represent a (hexahydro-1H-azepin-1-yl)methylene radical, the compounds of the present invention are similar to the penicillins described in British patent specification No. 1,293,590.

In the latter case, the compounds have side chains connected to the penam ring system by a group

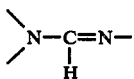

and these compounds are referred to as "amidinopenicillins". This type of side chain has recently been introduced into the chemistry of penicillins and it leads to compounds the activity of which at the bacterial wall is due to a mechanism different from that of the penicillins having traditional side chains, such as those defined above. The difference in their mode of action on the bacteria imparts a novel bacterial spectrum to the amidinopenicillins.

With regard to stereochemistry, the existence of three asymmetrical carbon atoms at $C_{3'}$, $C_{5'}$ and $C_{6'}$ should lead to the formation of 8 isomers which can be grouped into 4 racemic diastereoisomers. The kinetics of the reactions lead, in fact, to the formation of only three alpha-, beta- and gamma-racemates. The alpha-racemate is preferably isolated from the mixture, its relative configurations corresponding to those of penicillin, i.e. the S configuration at $C_{3'}$, and the R configuration at $C_{5'}$ and $C_{6'}$.

It is another object of the present invention to provide processes for preparing 6'-amino-spiro[cycloalkane-1,2'-penam]-3'-carboxylic acid derivatives of formula I and the pharmaceutically acceptable, non-toxic salts thereof.

The compounds of formula I, in which $R_1$ is a hydrogen atom and $R_2$ is a radical known from the chemistry of the penicillins, preferably a 2-phenylacetyl, 2,6-dimethoxybenzoyl, 2-amino-2-phenylacetyl, 5-methyl-3-phenyl-4-isoxazolecarbonyl or 2-carboxy-2-phenylacetyl radical, can be prepared by subjecting a corresponding 6'-amino-spiro[cycloalkane-1,2'-penam]-3'-carboxylic acid or an ester or a salt thereof, to an acylation reaction.

More particularly, the compounds of formula I, in which $R_1$ is a hydrogen atom and $R_2$ is a radical known from the chemistry of the penicillins, can be prepared by reacting a 6'-amino-spiro[cycloalkane-1,2'-penam]-3'-carboxylic acid of the formula:

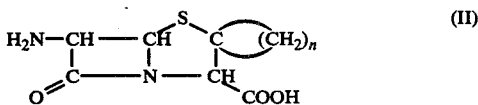

wherein n has the same meaning as above, or an ester or a salt thereof, with a halide of an organic monocarboxylic acid of the general formula $R_2OH$ or a functional equivalent thereof, wherein $R_2$ has the same meaning as above, this acid halide preferably being phenylacetyl chloride, 2,6-dimethoxybenzoyl chloride, 5-methyl-3-phenyl-4-isoxazolecarbonyl chloride, 2-phenylglycyl chloride or 2-carboxy-2-phenylacetyl chloride.

The functional equivalents of the above-mentioned acid halides which can be used as acylating agents for the primary amino radical of the 6'-amino-spiro[cycloalkane-1,2'-penam]-3'-carboxylic acids of formula II are, in particular, the acid anhydrides, including mixed anhydrides and especially the mixed anhydrides formed with stronger acids, such as the lower aliphatic monoesters or carbonic acid, the alkylsulfonic and arylsulfonic acids and acids having a more pronounced hindrance, such as diphenylacetic acid. In addition, an acid azide or an active ester or thioester (for example with p-nitrophenol, 2,4-dinitrophenol, thiophenol or thioacetic acid) may be used but, as an alternative, the free acid itself may be condensed with the 6'-amino-spiro[cycloalkane-1,2'-penam]-3'-carboxylic acid after the free acid has previously been activated by reaction with, for example, (chloromethylene)dimethylammonium chloride (see British patent specification No. 1,008,170 and Novak and Weichet, Experientia,XXI,6,(1965),360) or by means of enzymes, or with an N,N'-carbonyldiimidazole or an N,N'-carbonylditriazole (see British patent specification No. 967,108) or with a carbodiimide, for example, N,N'-dicyclohexylcarbodiimide (see example 4.4), N,N'-diisopropylcarbodiimide or N-cyclohexyl-N'-(2-morpholinoethyl)-carbodiimide (see Sheehan and Hess, J.Am.Chem.Soc. 77,(1955),1067) or an alkynylamine (see Buijle and Viehe, Angew.Chem., International Edition,3,(1964),582) or a ketene-imine (see Stevens and Munk, J. Am. Chem. Soc., 80, (1958), 4065) or an isoxazolium salt (see Woordward et al., J. Am. Chem. Soc. 83, (1961), 1010). Instead of the acid halides, the corresponding azolides can also be used.

When the starting compound used is an ester of the 6'-amino-spiro[cycloalkane-1,2'-penam]-3'-carboxylic acid, preferably the benzyl ester, the process of the present invention includes a second stage which comprises hydrogenolyzing the esters obtained to the corresponding acids. These esters only have a low antibacterial activity and are useful essentially as intermediates in the synthesis of the corresponding acids or salts.

The starting compounds may be, as desired, 6'-amino-spiro[cycloalkane-1,2'-penam]-3'-carboxylic acids or the salts or esters thereof. Nevertheless, we have found that, with regard to yield it is preferable to start in certain cases, with esters and, in other cases, with the acids themselves. Particularly when the substituent $R_2$ is a 2-phenylacetyl, 2,6-dimethoxybenzoyl or 2-amino-2-phenylacetyl radical, it is preferable to start with an ester, for example the benzyl ester, of the corresponding 6'-amino-spiro[cycloalkane-1,2'-penam]-3'-carboxylic acid, and to subject the resulting compound to a subsequent debenzylation reaction in order to obtain the free acid. When, on the other hand, the substituent $R_2$ is a 5-methyl-3-phenyl-4-isoxazolecarbonyl or 2-carboxy-2-phenylacetyl radical, it is preferable to start with the acid itself. Nevertheless, it must not be overlooked that the 6'-amino-spiro[cycloalkane-1,2'-penam]-3'-carboxylic acids are themselves always obtained from the corresponding esters, because it is necessary to protect the acid temporarily. In other words, the stage of conversion of the ester into the corresponding acid is not an additional stage because it is, in fact, simply shifted in the general synthesis process: in same cases, it is effected before the acylation reaction and, in other cases, after the acylation reaction.

Similarly, we have also found that there is a relationship between the nature of the substituents in the 2'-position and the ease of effecting the acylation of the ester first and then deprotection or of first effecting the deprotection and only then the acylation of the acid. Thus, when $R_2$ is a 2-amino-2-phenylacetyl radical, it is preferable to effect the acylation on the acid when n is 5, whereas it is preferable to effect it on the ester when n is 4.

The 6'-amino-spiro[cycloalkane-1,2'-penam]-3'-carboxylic acids of formula II and the alkali metal salts and esters thereof, which are the starting materials in the preparation of the new compounds of the present invention and also processes for preparing the same, are the subject matter of our Application Serial No. 800,082 filed concurrently herewith, to which reference is made for a detailed description.

Briefly, these starting compounds are prepared in the following manner:

(1) tert-Butyl 2-formyl-2-phthalimido-acetate of formula IV is reacted with an alpha-amino-1-mercapto-cycloalkaneacetic acid of formula V to give the alpha-isomer of a tert-butyl alpha-phthalimido-thia-azaspiroalkaneacetate of formula VI according to the following equation:

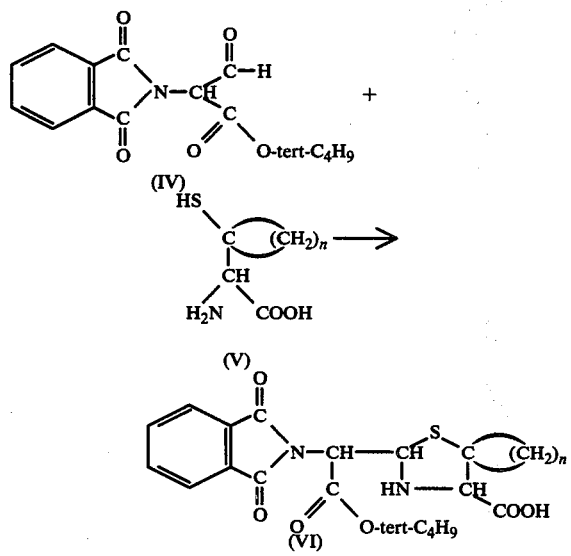

(2) the benzyl ester of formula VII is then prepared by reaction of the compound of formula VI with a benzyl halide according to the following equation:

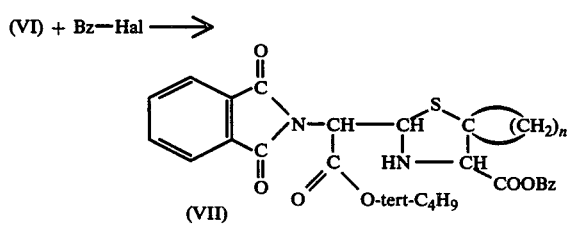

(3) the resulting compound of formula VII is then subjected to hydrazinolysis to give a tert-butyl alpha-amino-thia-azaspiroalkaneacetate of formula VIII according to the following equation:

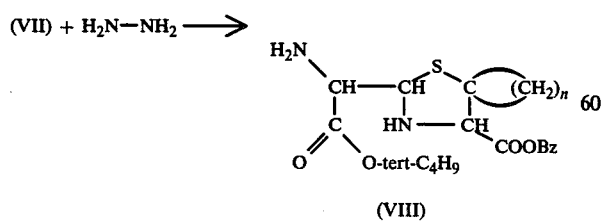

(4) the resulting compound of formula VIII is then subjected to partial acid hydrolysis in order to give a corresponding alpha-amino-thia-azaspiroalkane-acetic acid of formula IX, in the form of its hydrochloride, according to the following equation:

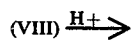

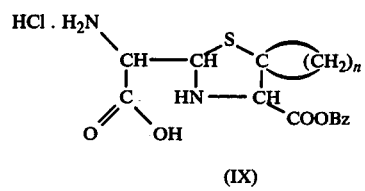

(5) the compound of formula IX, by reaction with trityl chloride, gives an alpha-tritylamino-thia-azaspiroalkaneacetic acid of formula X according to the following equation:

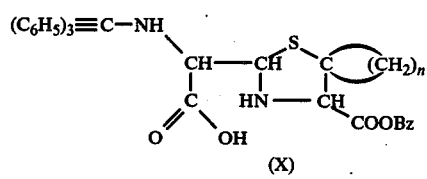

(6) the resulting compound of formula X is then cyclized with a carbodiimide (abbreviated as CI) to give a benzyl 6'-tritylamino-spiro[cycloalkane-1,2'-penam]-3'-carboxylate of formula XI, according to the following equation:

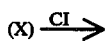

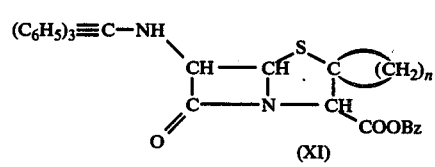

(7) the resulting compound of formula XI is then treated with p-toluenesulphonic acid to give a benzyl 6'-amino-spiro[cycloalkane-1,2'-penam]-3'-carboxylate p-toluenesulfonate according to the following equation:

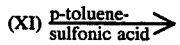

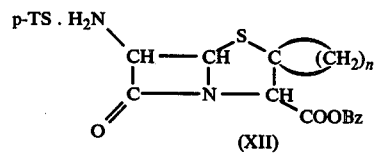

(8) the compound of formula XII is subjected to hydrogenolysis to give a 6'-amino-spiro[cycloalkane-1,2'-penam]-3'-carboxylic acid of formula (II) according to the following equation:

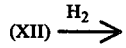

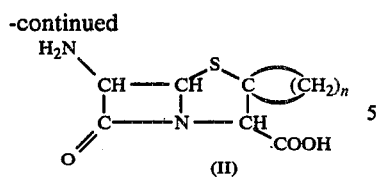

In the above formulae, Bz is a benzyl radical, p-TS represents p-toluenesulfonic acid, Hal is a halogen atom, for example a bromine atom, and n is a whole number of from 3 to 6.

With regard to the compounds used in the first stage, namely, the compounds of formulae IV and V, the process of preparing them is also indicated below.

The preparation of tert-butyl 2-formyl-2-phthalimido-acetate of formula IV is described in literature (Sheehan et al., J.Am.Chem.Soc. 76,(1954),158–160).

A method of preparing the alpha-amino-1-mercaptocycloalkaneacetic acids of formula V is, for example, as follows:

(1) An R′ 2-isocyanoacetate of formula XIII is condensed with a cycloalkanone of formula XIV, by means of a suspension of sodium hydride in tetrahydrofuran (THF), to give an R′ 2-formamido-2-cycloalkylidenacetate of formula XV, according to the following equation:

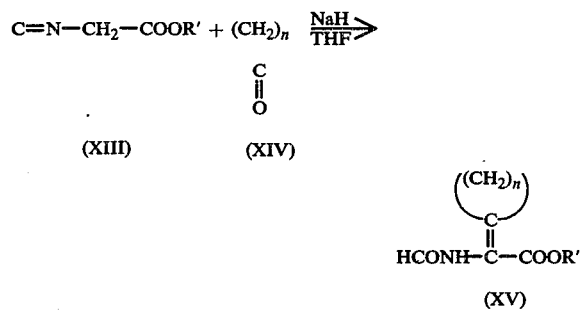

(2) the compound of formula XV, by treatment with phosphorus pentasulfide ($P_4S_{10}$), is cyclized to give an R′ thia-azaspiroalkenecarboxylate of formula XVI, according to the following equation:

(3) the resulting compound of formula XVI is then subjected to hydrolysis, accompanied by decyclization, to give an alpha-amino-1-mercaptocycloalkaneacetic acid of formula V according to the following equation:

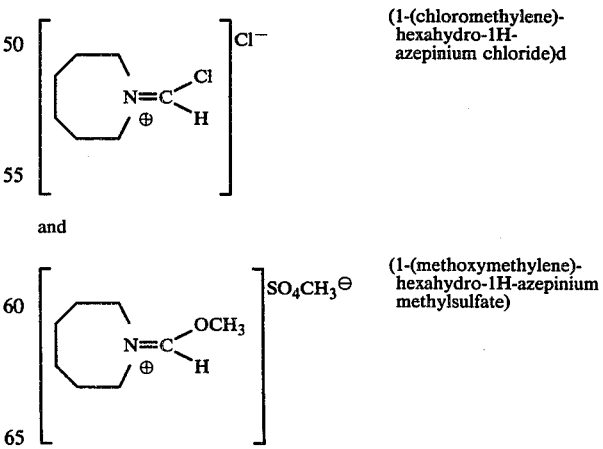

In the above formulae, R′ is a $C_1$-$C_3$ alkyl radical or a benzyl radical, and n is a whole number of from 3 to 6.

By "pharmaceutically acceptable, non-toxic salts", are to be understood, in particular, the salts of metals, such as sodium, potassium, calcium and aluminium, ammonium salts and the salts of amines, such as trialkylamines, particularly triethylamine, procaine, dibenzylamine, N-benzyl-beta-phenethylamine, L-ephenamine, N,N′-dibenzylethylenediamine, dehydroabietylamine, N,N′-bis-dehydroabietyl-ethylenediamine, the N-lower alkyl)-piperidines, such as N-ethylpiperidine, and, more generally, the salts already known for penicillins G and V (see Ullmann's Encyklopadie, loc.cit., p.653).

These salts can be prepared from the corresponding acids by known methods.

In the particular case in which $R_2$ is a 2-amino-2-phenylacetyl radical, the compounds of the present invention can be converted into their acid addition salts, for example with pharmaceutically acceptable non-toxic acids, such as acetic acid, citric acid, succinic acid, ascorbic acid, hydrochloric acid, hydrobromic acid, sulfuric acid or phosphoric acid.

The compounds of formula I, in which $R_1$ and $R_2$ represent together a bivalent radical $R_3$, preferably the (hexahydro-1H-azepin-1-yl)methylene radical, can be prepared by reacting a 6′-amino-spiro[cycloalkane-1,2′-penam]-3′-carboxylic acid of formula II or an ester or a salt thereof, with an activated derivative of a compound of the formula $R_3=O$ and preferably with an activated derivative of hexahydro-1H-azepin-1-carboxaldehyde.

The activated derivative of the compound $R_3=O$ is, for example and preferably the corresponding amide chloride obtained by reaction with oxalyl chloride or the complex obtained by reaction with dimethyl sulfate. Use is preferably made of the compounds, which are activated derivatives of hexahydro-1H-azepin-1-carboxaldehyde, having the following formulae:

(1-(chloromethylene)-hexahydro-1H-azepinium chloride)d and (1-(methoxymethylene)-hexahydro-1H-azepinium methylsulfate)

The present invention relates also to the use of the compounds of formula I and also of their pharmaceutically acceptable non-toxic salts, as antibacterial agents, as dietetic supplements for animal foodstuffs and as therapeutic agents for man and animals in the treatment of infectious diseases caused by Gram-positive and Gram-negative bacteria. Indeed, these compounds possess a very broad spectrum of antibacterial activity against both Gram-positive and Gram-negative bacteria.

Antibacterial activity

Numerous comparative tests have been carried out in respect of the biological activity of some compounds of the present invention towards various bacterial strains of the Gram-positive and Gram-negative type. The reference products used for the comparative tests are penicillin G, oxacillin, methicillin and ampicillin. First, some information is given below regarding the origins and characteristics of the bacterial strains used:

A. Gram-positive bacterial strains

*Sarcina lutea*

This is a Gram-positive coccus which is highly sensitive to penicillins. It is a typical example of a bacterium having no resistance mechanism towards penicillins and a model of an unprotected bacterial receptor. Consequently, the antibacterial activity upon this strain could be likened to a measure of the activity on a receptor.

*Staphylococcus aureus* 6538

This is also a Gram-positive coccus which is particularly sentitive to penicillins and which has a poor resistance mechanism. This strain of Staphylococcus is, therefore, representative of maximum sensitivity of the species.

*Staphylococcus aureus* 52149

This is a Gram-positive coccus for which the intrinsic sensitivity of the receptor is equivalent to that of the preceding strain but which produces a beta-lactamase typical of the species, making it resistant to all penicillins sensitive to hydrolysis.

B. Gram-negative bacterial strains

*Escherichia coli* B

This is a classical collection strain of *Escherichia coli* which produces very little beta-lactamase (of type I) and is therefore very sensitive to penicillins. With regard to the classification of the beta-lactamases, use is here made of that proposed by M. H. Richmond and R. B. Sykes in Advances in Microbial Physiology, 9, (1973), pages 43 and 45.

*Escherichia coli* B AMPI-R.

This is a mutant of the preceding strain, which we have produced. This strain, on the other hand, is a hyper-producer of beta-lactamase of type I already produced by the parent strain *Escherichia coli* B. It has an increased resistance to penicillins, which appears to be directly connected with the production of beta-lactamase.

*Escherichia coli* K 12–44

This is a mutant of *Escherichia coli* K 12, the typical reference parent strain of the species. This mutant does not produce beta-lactamase.

*Escherichia coli* K 12–44-TEM

This strain is obtained from a strain of *Escherichia coli* K 12–44 in which the episome TEM, which is, in particular, responsible for the production of a beta-lactamase of type III, has been transferred.

*Escherichia coli* K 12–44 S

This is a pleiotropic mutant of *Escherichia coli* K 12–44, which does not produce beta-lactamase and which we have produced. It is very sensitive to penicillins due to hyperpermeability.

C. Results of comparative activity tests

The minimum inhibiting concentration (abbreviated as MIC) has been determined for a certain number of compounds by the procedure described below.

The products are introduced in increasing concentration into a gelose culture medium in Petri dishes. A multiple inoculator is used for simultaneously depositing drops (i.e. a total of 10 microliters) of inoculum (suspension containing about $10^5$ bacteria per ml.) on the surface of the medium. After incubation at 37° C. for 24 hours, the growth of the bacteria is observed. By definition, the MIC is expressed (in micromoles) by the minimum concentration inhibiting the multiplication of the bacteria.

In all the results given below, the MIC is taken as being equal to 1 for the reference compounds and the activity figures indicated for the compounds tested are, therefore, relative values. This presentation of the results is the most correct and the most reproducible because, for the same bacterial strain, it is possible to observe different values of MIC if they are measured at different times. This is connected with "seasonal" variations of the strains and of their nutrient medium. Nevertheless, by way of indication, the absolute value of the MIC for the reference compounds, expressed in micromoles, is, in each case, also indicated in brackets.

| a) Comparative tests with penicillin G. | | | | |
|---|---|---|---|---|
| Strain used | penicillin G | Compound A | Compound B | Compound C |
| SARCINA LUTEA | 1 (0.01) | 1.6 | — | 2 |
| S.AUREUS 6538 | 1 (0.125) | 2.5 | 0.5 | 1 |
| E. COLI B | 1 (16) | 11 | 3.4 | 4 |
| S.AUREUS 52149 | 1 (3.1) | — | — | 1 |

Compound A: potassium 6'-(2"-phenylacetamido)-spiro[cyclohexane-1,2'-penam]-3'-carboxylate.
Compound B: potassium 6'-(2"-phenylacetamido)-spiro[cyclopentane-1,2'-penam]-3'-carboxylate.
Compound C: potassium 6'-(2"-phenylacetamido)-spiro[cyclobutane-1,2'-penam]-3'-carboxylate.

| b) Comparative tests with oxacillin. | | |
|---|---|---|
| Strain used | oxacillin | Compound D |
| S.AUEUS 6538 | 1 (1.25) | 1–0.65 |
| S.AUREUS 52149 | 1 (1.25) | 0.55 |

Compound D: sodium 6'-(5"-methyl-3"-phenyl-4"-isoxazole carboxamido)-spiro[cyclohexane-1,2'-penam]-3'-carboxylate.

| c) Comparative tests with methicillin. | | |
|---|---|---|
| Strain used | methicillin | Compound E | Compound F |
| S.AUEUS 6538 | 1 (3.1) | 1.25 | 0.4 | c) Comparative tests with methicillin.

| Strain used | methicillin | Compound E | Compound F |
|---|---|---|---|
| S. AUREUS 52149 | 1 (6.25) | 0.55 | 0.4 |

Compound E: sodium 6'-(2",6"-dimethoxybenzamido)-spiro[cyclohexane-1,2'-penam]-3'-carboxylate.
Compound F: sodium 6'-(2-2", 6"-dimethoxybenzamido)-spiro]cyclopentane-1,2'-penam]-3'-carboxylate.

d) Comparative tests with ampicillin.

| Strain used | ampicillin | Compound G | Compound H |
|---|---|---|---|
| S.AUREUS 6538 | 1 (0.08–0.2) | 1 | 1 |
| E.COLI B | 1 (1.3) | 30 | 3.8 |
| E.COLI B AMPI-R | 1 (27.5–56) | >2 | 2 |
| E.COLI K 12-44 | 1 (4.5–4.9) | 10 | 4.2 |
| E.COLI K 12-44-TEM | 1 | 1 | 1 |
| E.COLI K 12-44 S | 1 (1.25) | — | 2.6 |

Compound G: sodium 6'-(2"-amino-2"-phenylacetamido)-spiro[cyclohexane-1,2'-penam]-3'-carboxylate.
Compound H: 6'-(2"-amino-2"-phenylacetamido)-spiro]cyclopentane-1,2'penam]-3'-carboxylic acid.

D. Posology and fields of use

The compounds of the present invention can be administered orally or parenterally.

The limits indicated hereinbelow are only approximate because they are essentially deduced from the MIC values. For the values in vivo, other factors are involved, for example, blood level, resorption, metabolization and elimination, the influence of which can be determined only by clinical experience. This has the practical consequence that, with an equal MIC value, two compounds may, nevertheless, have a different posology.

(a) Homologues of penicillin G.

Pencillin G is used in the treatment of infections caused by non-resistant Gram-positive bacteria. The posology is between 0.2 and 3.0 g. per day.

Compound A, for the same use, can be used in doses between about 0.5 and 7.0 g. per day.

Similarly, compound B can be used in doses between 0.1 and 1.5 g. per day, and compound C in doses between 0.2 and 3.0 g. per day.

(b) Homologues of oxacillin.

Oxacillin is used in the treatment of infections due to penicillin-resistant Staphylococci producing beta-lactamase. The posology is between 4 and 8 g. per day.

For the same use, compound D can be used in doses between 2 and 4 g. per day.

(c) Homologues of methicillin.

In the same field of use as oxacillin, the posology is about 2 g. per day.

For the same use, compound E may be administered in doses ranging from 1 to 2 g. per day, compound F in a dose of about 1 g. per day.

(d) Homologues of ampicillin.

Ampicillin is used in the treatment of infections caused by a very broad spectrum of bacteria, which covers not only Gram-positive but also Gram-negative bacteria. The posology is between 0.2 and 2 g. per day.

Compound G, which acts essentially on Gram-positive bacteria, can be used in doses between 0.5 and 1 g. per day. It also has activity against Gram-negative bacteria but in doses which are therapeutically too high.

On the other hand, compound H behaves more closely to ampicillin, with a posology of 0.5 to 2 g. per day for Gram-positive bacteria and a posology of from 2 to 8 g. for Gram-negative bacteria.

The following Examples are given for the purpose of illustrating the present invention.

EXAMPLE 1

Preparation of 6'-(2"-phenylacetamido)-spiro[cycloalkane-1,2'-penam]-3'-carboxylic acids and their derivatives 1.1. Preparation of benzyl 6'-(2"-phenylacetamido)-spiro[cycloalkane-1,2'-penam]-3'-carboxylates.

(a) Benzyl 6'-(2"-phenylacetamido)-spiro[cyclohexane-1,2'-penam]-3'-carboxylate.

A solution of 107 mg. (0.00106 mole) of triethylamine in 5 ml. dichloromethane is added to a suspension of 550 mg. (0.00106 mole) of benzyl 6'-amino-spiro[cyclohexane-1,2'-penam]-3'-carboxylate p-toluenesulfonate (prepared by the method described in Example V.1 of our Application Serial No. 800,082 filed concurrently herewith) in 5 ml. of anhydrous dichloromethane. The mixture is cooled with a bath kept between 0 and −5° C. and then, over a period of one hour, there are alternately added, in small amounts, to the resulting clear solution 183 mg. (0.00118 mole) of phenylacetyl chloride dissolved in 5 ml. of dichloromethane, on the one hand, and 118 mg. (0.00119 mole) of triethylamine dissolved in 5 ml. dichloromethane, on the other hand. The reaction mixture is left for 2 hours in a refrigerator and then washed successively with 0.5 N hydrochloric acid, 5% aqueous sodium hydrogen carbonate solution and finally with water. The organic phase is dried and evaporated. The residue is crystallized from a diethyl ether-hexane mixture (1:5) and 450 mg. (0.00097 mole) of benzyl 6'-(2"-phenylacetamido)-spiro[cyclohexane-1,2'-penam]-3'-carboxylate are obtained. Yield: 91.5%. MP. 114°–115° C.

Analysis (in % by weight) for $C_{26}H_{28}N_2O_4S$ (M.W. 464): Calculated: C, 67.24; H, 6.03; N, 6.03. Found: C, 67.30; H, 6.15; N, 6.10.

Infra-red spectrum in KBr (in $cm^{-1}$):
3250 (NH)
1775 (CO beta-lactam)
1750 (CO ester)
1643 (CO amide)
753 and 692 (monosubstituted phenyl)

| NMR spectrum (CDCl$_3$-tetramethylsilane, abreviated as TMS): | |
|---|---|
| 1.5 ppm multiplet | 10H (cyclohexyl) |
| 3.63 ppm singlet | 2H (CH$_2$ of the phenylacetyl group) |
| 4.48 ppm singlet | 1H (H$_{3'}$) |
| 5.15 ppm singlet | 2H (CH$_2$ of the benzyl group) |
| 5.45 ppm doublet | (J = 4.2 cycles per second) 1H  (H$_{5'}$) |
| 5.63 ppm doublet | (J = 4.2 cycles per second) 1H  and H$_{6'}$) |
| 6.10 ppm multiplet | 1H (NH) |
| 7.31 ppm singlet | 10H (2 benzene rings) |
| 7.35 ppm singlet | |

Mass spectrum: molecular ion at m/e 464
345 ($M^+$ - $C_6H_5$—$CH_2CO$)
290 (metastable ion m* at 181.25 with 464–174)
91 (100% and metastable ion m* at 28.56, with 290–199)

(b) Benzyl 6'-(2"-phenylacetamido)-spiro[cyclopentane-1,2'-penam]-3'-carboxylate.

This compound is obtained in the same manner as the preceding compound from benzyl 6'-amino-spiro[cyclopentane-1,2'-penam]-3'-carboxylate p-toluenesulfonate (prepared by the method described in Example V.2 of our Application Serial No. 800,082 filed concurrently herewith).

Analysis (in % by weight) for $C_{25}H_{26}N_2O_4S$ (M.W. 450): Calculated: C 66.66 H 5.78 N 6.22 Found: 67.00 6.10 6.32

I.R. spectrum in KBr (in cm$^{-1}$):
| | |
|---|---|
| 3240 | (NH) |
| 1775 | (CO beta-lactam) |
| 1724 | (CO ester) |
| 1659 | (CO amide) |
| 720 and 690 | (monosubstituted phenyl) |

NMR (CDCl$_3$-TMS):
| | | |
|---|---|---|
| 1.7 ppm | multiplet | 8H (cyclopentyl) |
| 3.65 ppm | singlet | 2H (CH$_2$ of the phenylacetyl group) |
| 4.60 ppm | singlet | 1H (H$_3$) |
| 5.18 ppm | singlet | 2H (CH$_2$ of the benzyl group) |
| 5.6 ppm | multiplet | 2H (H$_5$ and H$_6$) |
| 6.1 ppm | multiplet | 1H (NH) |
| 7.35 ppm | singlet | 10H (2 benzene rings) |

Mass spectrum: molecular ion at m/e 450
276 (450–174 corresponds to

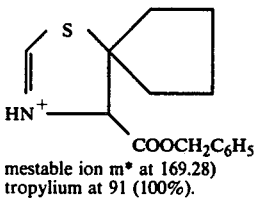

mestable ion m* at 169.28)
tropylium at 91 (100%).

(c) benzyl 6'-(2''-phenylacetamido)-spiro[cyclobutane-1,2'-penam]-3'-carboxylate.

This compound is prepared in the same manner as the preceding compounds from benzyl 6'-amino-spiro[cyclobutane-1,2'-penam]-3'-carboxylate p-toluenesulfonate (prepared by the method described in Example V.3 of our Application Serial No. 800,082 filed concurrently herewith). Yield: 78%. M.P. 105°–6° C. (ethyl acetate/hexane).

Analysis (in % by weight) for $C_{24}H_{24}N_2O_4S$ (M.W. 436): Calculated: C 66.06 H 5.50 N 6.42 Found: 65.99 5.50 6.40

I.R. spectrum in KBr:
| | |
|---|---|
| 3245 cm$^{-1}$ | (NH) |
| 1790 cm$^{-1}$ | (C=O beta-lactam) |
| 1729 cm$^{-1}$ | (C=O benzyl ester) |
| 1645 cm$^{-1}$ | (C=O amide) |
| 759 and 698 cm$^{-1}$ | (monosubstituted phenyl) |

NMR (CDCl$_3$-TMS):
| | | |
|---|---|---|
| 1.5–2.6 ppm | multiplet | 6H (cyclobutyl) |
| 3.7 ppm | singlet | 2H (CH$_2$ of the phenylacetyl group) |
| 4.8 ppm | singlet | 1H (H$_3$) |
| 5.2 ppm | singlet | 2H (CH$_2$ of the benzyl group) |
| 5.4 ppm | doublet | (J=4 cycles per second) 1H (H$_6$) |
| 5.65 ppm | doublet | (J=4 cycles per second) |
| 6.1 ppm | "doublet" | (J=8 cycles per second) 1H (H$_5$) 1H (NH) |
| 7.35 ppm | singlet | 10H (2 benzene rings) |

Mass spectrum: m/e 436 (molecular ion)

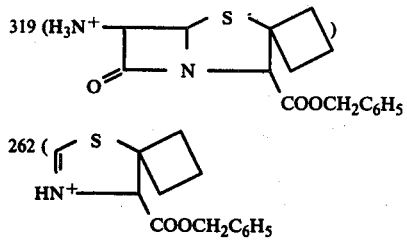

(d) benzyl 6'-(2'''-phenylacetamido)-spiro[cycloheptane-1,2'-penam]-3'-carboxylate This compound is prepared in the same manner as the preceding compounds.

1.2. Preparation of 6'-(2''-phenylacetamido)-spiro[cycloalkane-1,2'-penam/-3'-carboxylic acids.

(a) 6'-(2''-Phenylacetamido)-spiro[cyclohexane-1,2'-penam]-3'-carboxylic acid (potassium salt).

450 mg. of palladium/carbon catalyst (10% Pd) are added to a solution of 320 mg. (0.008 mole) of benzyl 6'-(2''-phenylacetamido)-spiro[cyclohexane-1,2'-penam]-3'-carboxylate in 30 ml. of ethyl acetate and hydrogenolysis is carried out for 5 hours at ambient temperature under a hydrogen pressure of 3.3 atmospheres. The reaction mixture is then filtered and washed with ethyl acetate, 50 ml. of water are added and the pH of the aqueous phase is adjusted with a dilute aqueous solution of potassium hydroxide to 7.2. The aqueous phase is decanted, subjected to a partial vacuum to eliminate the last traces of ethyl acetate and lyophilized. 0.2 g. of potassium 6'-(2''-phenylacetamido)-spiro[cyclohexane-1,2'-penam]-3'-carboxylate is thus obtained. M.P. 218°–200° C. (decomposition). Yield: 60.5%.

Analysis (in % by weight) for $C_{19}H_{21}KN_2O_4S$ (M.W. 412): Calculated: C, 55.34; H, 5.10; N, 6.90. Found: C, 49.50; H, 4.90; N, 6.13.

I.R. spectrum (in cm$^{-1}$) in KBr-
| | |
|---|---|
| 3370 | (NH) |
| 1762 | (CO beta-lactam) |
| 1655 | (CO amide) |
| 755 and 692 | (monosubstituted phenyl) |

NMR spectrum (D$_2$O-sodium dimethyl-2,2-sila-2-pentane sulfonate, abbreviated as DSS):
| | | |
|---|---|---|
| 1.8 ppm | multiplet | 10H (cyclohexyl) |
| 3.65 ppm | singlet | 2H (CH$_2$ of the phenylacetyl) |
| 4.25 ppm | singlet | 1H (H$_3$) |
| 5.42 ppm | quartet | (J=4.5 cycles per second) 2H (H$_5$ and H$_6$) |
| 7.35 ppm | singlet | 5H (phenyl) |

(b) 6'-(2''-Phenylacetamido)-spiro[cyclopentane-1,2'-penam]-3'-carboxylic acid (potassium salt).

This compound is prepared in the same manner as the previous compound, in a yield of 69.7%. M.P. 209°–211° C.

Analysis (in % by weight) for $C_{18}H_{19}KN_2O_4S$ (M.W. 398) Calculated: C, 51.9; H, 5.05; N, 6.72. Found: C, 50.9; H, 4.18; N, 6.66.

| I.R. spectrum (in cm$^{-1}$) in KBr: | |
|---|---|
| 3354 | (NH) |
| 1765 | (CO beta-lactam) |
| 1655 | (CO amide) |
| 718 and 690 | (monosubstituted phenyl) |

| NMR spectrum (D$_2$O—DSS): | | |
|---|---|---|
| 1.75 ppm | multiplet | 8H (cyclopentyl) |
| 3.67 ppm | singlet | 2H (CH$_2$ of the phenylacetyl group) |
| 4.4 ppm | singlet | 1H (H$_{3'}$) |
| 5.45 ppm | quartet | (J=4 cycles per second 2H (H$_{5'}$ and H$_{6'}$) |
| 7.37 ppm | singlet | 5H (phenyl) |

(c) 6'-(2"-phenylacetamido)-spiro[cyclobutane-1,2'-penam]-3'-carboxylic acid (potassium salt).

This compound is prepared in the same manner as the preceding compound, with the only difference that the pH of the aqueous phase is adjusted to 8.9. Yield: 57%. M.P. 197°–8° C. (decomposition).

Analysis (in % by weight) for C$_{27}$H$_{30}$N$_2$O$_6$S (M.W. 510): Calculated: C, 63.53; H, 5.88; N, 5.49. Found: C, 63.40; H, 5.94; N, 5.40.

| I.R. spectrum (KBr) | |
|---|---|
| 3400 cm$^{-1}$ | (H$_2$O) |
| 1762 cm$^{-1}$ | (C=O beta-lactam) |
| 1655 cm$^{-1}$ | (C=O amide) |
| 1595 cm$^{-1}$ | (C=O of COO$^-$) |
| 720 and 685 cm$^{-1}$ | (monosubstituted phenyl) |

| NMR spectrum (D$_2$O—DSS): | | |
|---|---|---|
| 1.5–2.7 ppm | multiplet | 6H (cyclobutyl) |
| 3.72 ppm | singlet | 2H (CH$_2$ of the phenylacetyl group) |
| 4.6 ppm | singlet | 1H (H$_{3'}$) |
| 5.45 ppm | quartet | (J=4 cycles per second) 2H (H$_{5'}$ and H$_{6'}$) |
| 7.35 ppm | singlet | 5H (phenyl) |

(d) 6'-(2"-phenylacetamido)-spiro[cycloheptane-1,2'-penam]-3'-carboxylic acid (potassium salt).

This compound is prepared in the same manner as the preceding compound.

EXAMPLE 2

Preparation of 6'-(2",6"-dimethoxybenzamido)-spiro[cycloalkane-1,2'-penam]-3'-carboxylic acids and their derivatives 2.1 Preparation of benzyl 6'-(2",6"-dimethoxybenzamido)-spiro[cycloalkane-1,2'-penam]-3'-carboxylates.

(a) Benzyl 6'-(2",6"-dimethoxybenzamido)-spiro[cyclohexane-1,2'-penam]-3'-carboxylate.

A solution of 202 mg. (0.002 mole) of triethylamine in 10 ml. of anhydrous dichloromethane is added to a suspension of 1.04 g. (0.002 mole) of benzyl 6'-aminospiro[cyclohexane-1,2'-penam]-3'-carboxylate p-toluenesulfonate (prepared as indicated in Example 1.1 ((a)) in 50 ml. of anhydrous dichloromethane. The reaction mixture is cooled by means of an ice-bath and there are alternately added in portions and with magnetic agitation, over a period of half an hour, on the one hand, a solution of 441 mg. (0.0022 mole) of 2,6-dimethoxybenzoyl chloride in 10 ml. of anhydrous dichloromethane and, on the other hand, a solution of 223 mg. (0.0022 mole) of triethylamine in 10 ml. of anhydrous dichloromethane. Stirring is continued for one hour at ambient temperature and the reaction mixture is then washed successively with 0.05 N hydrochloric acid, 5% aqueous sodium hydrogen carbonate solution and twice with water. The organic phase is dried and evaporated. The residue is crystallized from diethyl ether-hexane (1:1) to give 0.9 g. of benzyl 6'-(2",6"-dimethoxybenzamido)-spiro[cyclohexane-1,2'-penam]-3'-carboxylate. M.P. 152°–153° C. Yield: 88%.

| Infra-red spectrum in KBr (in cm$^{-1}$): | |
|---|---|
| 3355 | (NH) |
| 1767 | (CO beta-lactam) |
| 1737 | (CO ester) |
| 1664 | (CO amide) |
| 782 | (trisubstituted phenyl) |
| 747 and 696 | (monosubstituted phenyl) |

| NMR spectrum (CDCl$_3$—TMS): | | |
|---|---|---|
| 1.60 ppm | multiplet | 10H (cyclohexyl) |
| 3.80 ppm | singlet | 6H (2 × —OCH$_3$) |
| 4.52 ppm | singlet | 1H (H$_{3'}$) |
| 5.20 ppm | singlet | 2H (CH$_2$ of the benzyl group) |
| 5.55 ppm | doublet | (J=4 cycles per second) 1H (H$_{5'}$) |
| 5.92 ppm | double doublet | J=4 and 10 cycles per second) 1H (H$_{6'}$) |
| 6.48 ppm | doublet | 1H (NH) |

Mass spectrum: molecular ion at m/e 510
290 (typical fragment/

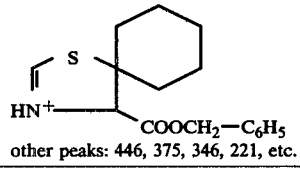

other peaks: 446, 375, 346, 221, etc.

(b) Benzyl 6'-(2",6"-dimethoxybenzamido)-spiro[cyclopentane-1,2'-penam]-3'-carboxylate.

This compound is prepared, in the same manner as the proceding compound from benzyl 6'-amino-spiro[cyclopentane-1,2'-penam]-3'-carboxylate p-toluenesulfonate (prepared as indicated in Example 1.1 ((b)). Yield: 57%. M.P. 167°–168° C.

Analysis (in % by weight) for C$_{26}$H$_{28}$N$_2$O$_6$S (M.W. 496): Calculated: C, 62.9; H, 5.64; N, 5.64. Found: C, 62.4; H, 6.08; N, 5.42.

| Infra-red spectrum in KBr (in cm$^{-1}$): | |
|---|---|
| 3350 | (NH) |
| 1755 | (beta-lactam) |
| 1732 | (CO ester) |
| 1672 | (CO amide) |
| 773 | (trisubstituted phenyl) |

-continued

| 742, 686 | (monosubstituted phenyl) | |
|---|---|---|
| NMR spectrum (CDCl₃—TMS) | | |
| 1.78 ppm | multiplet | 8H (cyclopentyl) |
| 3.83 ppm | singlet | 6H (2 × —OCH₃) |
| 4.7 ppm | singlet | 1H (H₃') |
| 5.23 ppm | singlet | 2H (CH₂ of the benzyl) |
| 5.65 ppm | doublet | (J=4.5 cycles per second) 1H (H₅') |
| 6.6 ppm | doublet | 1H (H₆') |
| 6.6 ppm | doublet | 2H (H₃'' and H₅'') |
| 7.30 ppm | multiplet | 1H (H₄'') |
| 7.40 ppm | singlet | (phenyl) |

Mass spectrum:
molecular ion at 496
usual fragment at 276
other peaks at 468, 464, 452, 362, 221.

The following compounds are prepared in the same manner:

(c) Benzyl 6'-(2'',6''-dimethoxybenzamido)-spiro[cyclobutane-1,2'-penam]-3'-carboxylate;

(d) Benzyl 6'-(2'',6''-dimethoxybenzamido)-spiro[cycloheptane-1,2'-penam]-3'-carboxylate.

2.2 Preparation of 6'-(2'',6''-dimethoxybenzamido)-spiro[cycloalkane-1,2'-penam]-3'-carboxylic acids (a) 6'-(2'',6''-dimethoxybenzamido)-spiro[cyclohexane-1,2'-penam]-3'-carboxylic acid (sodium salt).

1.5 g. of palladium/carbon catalyst (10% Pd) are added to a solution of 820 mg. (0.0016 mole) of benzyl 6'-(2'',6''-dimethoxybenzamido)-spiro[cyclohexane-1,2'-penam]-3'-carboxylate in 100 ml. of ethyl acetate and hydrogenolysis is carried out for 2 hours at ambient temperature at a hydrogen pressure of 2 atmospheres. The reaction mixture is filtered, washed with a mixture of acetic acid and dichloromethane (3:7) and evaporated under a high vacuum to give 680 mg. of crude product. This product is taken up in 30 ml. of ethyl acetate and 100 ml. of water and the solution obtained is adjusted to pH 7, while stirring and under a nitrogen atmosphere, with 2N aqueous sodium hydroxide solution. The product is then lyophilized. 540 mg. of sodium 6'-(2'',6''-dimethoxybenzamido)-spiro[cyclohexane-1,2'-panam]-3'-carboxylate are thus obtained. M.P. 213°-215° C. Yield: 68%.

Analysis (in % by weight) for C₂₀H₂₃N₂O₆Na.3H₂O: Calculated: C, 48.39; H, 5.85; N, 5.65. Found: C, 48.20; H, 5.80; N, 5.00.

| Infra-red spectrum in KBr (in cm⁻¹): | | |
|---|---|---|
| 3400 | (H₂O) | |
| 1756 | (CO beta-lactam) | |
| 775 | (trisubstituted phenyl) | |
| NMR spectrum (in dimethylsulfoxide; abbreviated as DMSO—TMS): | | |
| 1.70 ppm | multiplet | 10H (cyclohexyl) |
| 3.57 ppm | singlet | 6H (3 × H₂O) |
| 3.75 ppm | singlet | 6H (2 × —OCH₃) |
| 3.98 ppm | singlet | 1H (H₃') |
| 5.55 ppm | multiplet | (J=4 and 8 cycles per second) 2H (H₅' and H₆') |
| 6.70 ppm | "doublet" | (J=8 cycles per second 2H CH₃'' and H₅'') |
| 7.35 ppm | triplet | (J=8 cycles per second) 1H (H₄'') |
| 8.45 ppm | doublet | (J=8 cycles per second) 1H (NH) |

(b) 6'-(2'',6''-dimethoxybenzamido)-spiro[cyclopentane-1,2'-penam]-3'-carboxylic acid (sodium salt).

This compound is prepared in the same manner as the preceding compound, in a yield of 90%. M.P. 208°-210° C. (decomposition).

Analysis (in % by weight) for C₁₉H₂₁NaN₂O₆S.2H₂O (M.W. 464): Calculated: C, 49.13; H, 5.38; N, 6.03. Found: C, 48.00; H, 4.91; N, 6.05.

| Infra-red spectrum in KBr (in cm⁻¹): | | |
|---|---|---|
| 3390 | (H₂O) | |
| 1755 | (CO beta-lactam) | |
| 1665 | (CO amide) | |
| 775-715 | (trisubstituted phenyl) | |
| NMR spectrum (in D₂O—DSS): | | |
| 1.80 ppm | multiplet | 8H (cyclopentyl) |
| 3.92 ppm | singlet | 6H (2 × —OCH₃) |
| 4.60 ppm | singlet | 1H (H₃') |
| 4.70 ppm | doublet | 1H (H₅') |
| 5.65 ppm | doublet | 2H (H₆') |
| 6.80 ppm | doublet | 2H (H₃'' and H₅'') |
| 7.50 ppm | triplet | 1H (H₄''( |

The sodium salts of the following acids are prepared in the same manner:

(c) 6'-(2'',6''-dimethoxybenzamido)-spiro[cyclobutane-1,2'-penam]-3'-carboxylic acid.

(d) 6'-(2'',6''-dimethoxybenzamido)-spiro[cycloheptane-1,2'-penam]-3'-carboxylic acid.

EXAMPLE 3

Preparation of 6'-(5''-methyl-3''-phenyl-4''-isoxazolecarboxamido)-spiro[cycloalkane-1,2'-penam]-3'-carboxylic acids and their derivatives 3.1. 6'-(5''-methyl-3''-phenyl-4''-isoxazolecarboxamido)-spiro[cyclohexane-1,2'-penam]-3'-carboxylic acid (sodium salt).

384 mg. (0.0015 mole) of 6'-amino-spiro[cyclohexane-1,2'-penam]-3'-carboxylic acid (prepared by the method described in Example VI.1 of our Application Ser. No. 800,082 filed concurrently herewith) are suspended in 2 ml. of water free of carbon dioxide. 15 ml. of a 10⁻⁴N aqueous sodium hydroxide solution are added thereto at 0° C. in order to bring the pH to 7.8. The solution becomes clear. At a temperature of about −5° C., 332 mg. (0.0015 mole) of 5-methyl-3-phenyl-4-isoxazolecarbonyl chloride, dissolved in 10 ml. of acetone, are added. After this addition, a clear solution is obtained which is kept under magnetic agitation for 1 hour at 0° C. 10 g. of sodium chloride are then added and the mixture is extracted with benzene. The organic phase obtained in this manner is dried over anhydrous sodium sulfate and evaporated to dryness to give 700 mg. of crude product. The sodium salt is obtained by dissolving the acid in 2 ml. of anhydrous dichloromethane, to which is added a solution of 207 mg. (0.0015 mole) of the sodium salt of 2-ethylbutyric acid in 2 ml. of isopropanol. 100 ml. of diethyl ether are then added and the resulting precipitate is filtered and washed with diethyl ether. 500 mg. of sodium 6'-(5''-methyl-3''-phenyl-4''-isoxazolecarboxamido)-spiro[cyclohexane-1,2'-penam]-3'-carboxylate are thus obtained. M.P. 194°-197° C. (decomposition). Yield: 66.6%.

Analysis (in % by weight) for C₂₂H₂₂N₃NaO₅S.2H₂O (M.W. 499): Calculated: C, 52.9; H, 5.21; N, 8.41. Found: C, 53.1; H, 4.65; N, 7.11.

| Infra-red spectrum in KBr (in cm⁻¹): | | |
|---|---|---|
| 3370 | (H₂O) | |
| 1756 | (CO beta-lactam) | |
| 1650 | (CO amide) | |
| 759 and 690 | (monosubstituted phenyl) | |
| NMR spectrum (in D₂O—DSS): | | |
| 1.65 ppm | multiplet | 10H (cyclohexyl) |

-continued

| | | |
|---|---|---|
| 2.60 ppm | singlet | 3H (CH₃ at 5″) |
| 4.20 ppm | singlet | 1H (H₃') |
| 5.55 ppm | quartet | (J=4.5 cycles per second) 2H (H₅' and H₆') |
| 7.53 ppm | singlet | 5H (phenyl) |

The sodium salts of the following compounds are prepared in the same manner:

3.2. 6'-(5″-methyl-3″-phenyl-4″-isoxazolecarboxamido)-spiro[cyclobutane-1,2'-penam]-3'-carboxylic acid.

3.3. 6'-(5″-methyl-3″-phenyl-4″-isoxazolecarboxamido)-spiro[cyclopentane-1,2'-penam]-3'-carboxylic acid.

3.4. 6'-(5″-methyl-3″-phenyl-4″-isoxazolecarboxamido)-spiro[cycloheptane-1,2'-penam]-3'-carboxylic acid.

EXAMPLE 4

Preparation of 6'-(2″-amino-2″-phenylacetamido)-spiro[cycloalkane-1,2'-penam]-3'-carboxylic acids and their derivatives 4.1. 6'-(2″-amino-2″-phenylacetamido)-spiro[cyclohexane-1,2'-penam]-3'-carboxylic acid (and its sodium salt).

202 mg. (0.002 mole) of triethylamine in 1 ml. of anhydrous dichloromethane and 134 mg. (0.0011 mole) of N,N-dimethylaniline in 1 ml. of anhydrous dichloromethane are added under an atmosphere of nitrogen and at ambient temperature to a suspension of 256 mg. (0.001 mole) of 6'-amino-spiro[cyclohexane-1,2'-penam]-3'-carboxylic acid (prepared as indicated in Example 3.1) in 4 ml. of anhydrous dichloromethane. The mixture is stirred magnetically for 20 hours at ambient temperature and thus the solubilization is practically complete. The mixture is cooled to 12°-15° C. and 217 mg. (0.002 mole) of trimethylchlorosilane in 1 ml. of anhydrous dichloromethane are added dropwise. A white precipitate is formed which dissolves when the temperature comes back to 20° C. The reaction mixture is heated under reflux for 45 minutes. After this mixture has been cooled to −10° C., 206 mg. (0.001 mole) of 2-phenylglycyl chloride hydrochloride are added in portions over a period of 20 minutes. The mixture is stirred for half an hour and then placed in a refrigerator for 2 hours. The reaction mixture is then poured into 5 ml. of water, decanted and the aqueous phase, which has a pH of 1.7, is made up to 10 ml. and the pH adjusted to between 1.8 and 2 with 1N hydrochloric acid. The resulting white solid is filtered off. The filtrate is cooled to 2° C. and 240 mg. of (0.00125 mole) naphtalenesulfonic acid in 1 ml. of water are added thereto. The pH is adjusted to between 1.5 and 1.8. A white solid crystallizes out and stirring is continued for some hours at 2° C. The solid is filtered off, washed with iced water and with ethyl acetate and then dried in vacuo. 300 mg. of the 2-naphtalenesulfonic acid salt of 6'-(2″-amino-2″-phenylacetamido)-spiro[cyclohexane-1,2'-penam]-3'-carboxylic acid are thus obtained. The base is liberated by adding 52 mg. (0.0005 mole) of triethylamine and treating the mixture at about 70°-80° C. for 15 minutes. The resulting product is filtered off and washed with a mixture of isopropanol and water (85:15). 60 mg. of 6'-(2″-amino-2″-phenylacetamido)-spiro[cyclohexane-1,2'-penam]-3'-carboxylic acid are thus obtained. M.P. 211°-213° C. (decomposition). 40 mg. of this acid are converted into the sodium salt by treatment with a solution of 8.7 mg. of sodium hydrogen carbonate in 3 ml. of water.

A very small amount of insoluble matter is eliminated by centrifuging and the solution is lyophilized. Partially hydrated sodium 6'-(2″-amino-2″-phenylacetamido)-spiro[cyclohexane-1,2'-penam]-3'-carboxylate is obtained, M.P. 213°-216° C. (decomposition).

| Infra-red spectrum in KBr (in cm⁻¹): | | |
|---|---|---|
| 3400 | (H₂O and NH₂) | |
| 1755 | (CO beta-lactam) | |
| 1660 | (CO amide) | |
| 1600 | (CO acid) | |
| 690 | (monosubstituted phenyl) | |
| NMR spectrum (D₂O—DSS): | | |
| 1.70 ppm | multiplet | ± 10H (cyclohexyl) |
| 2.9 ppm | multiplet | 2H (NH₂) |
| 4.25 ppm | singlet | 1H (H₃') |
| 5.45 ppm | singlet | 2H (H₅' and H₆') |
| 7.45 ppm | singlet | 5H (phenyl) |

The following acids and also their sodium salts are prepared in the same manner:

4.2. 6'-(2″-amino-2″-phenylacetamido)-spiro[cyclobutane-1,2'-penam]-3'-carboxylic acid.

4.3. 6'-(2″-amino-2″-phenylacetamido)-spiro[cycloheptane-1,2'-penam]-'-carboxylic acid.

4.4. Preparation of 6'-(2″-amino-2″-phenylacetamido)-spiro[cyclopentane-1,2'-penam]-3'-carboxylic acid.

(a) Benzyl 6'-(2″-benzyloxycarbonylamino-2″-phenylacetamido)-spiro[cyclopentane-1,2'-penam]-3'-carboxylate.

A solution of 101 mg. (0.001 mole) of triethylamine in 5 ml. anhydrous dichloromethane is added at ambient temperature to a suspension of 504 mg. (0.001 mole) of benzyl 6'-amino-spiro[cyclopentane-1,2'-penam]-3'-carboxylate p-toluenesulfonate (prepared by the method described in Example V.2 of our Application Serial No. 800,082 filed concurrently herewith) in 20 ml. of distilled anhydrous dichloromethane. 313 mg. (0.0011 mole) of N-(benzyloxycarbonyl)-2-phenyl-D-(−)-glycine are added to the resulting clear solution after the latter has been cooled to about 0° C. by means of an ice-bath. After stirring for 5 minutes, a solution of 226 mg. (0.0011 mole) of N,N'-dicyclohexylcarbodiimide in 10 ml. of anhydrous dichloromethane is added dropwise over a period of 45 minutes. The reaction mixture is allowed to return gradually to ambient temperature and stirring is maintained overnight. The reaction mixture is then filtered to separate the dicyclohexylurea formed and the filtrate is washed successively with an 0.1 N aqueous solution of hydrochloric acid, water, a 5% aqueous solution of sodium hydrogen carbonate (NaHCO₃) and finally with water.

The filtrate is dried over anhydrous sodium sulfate and evaporated to dryness; 950 mg. of crude product are thus obtained. This mixture is purified by chromatography on silica (eluant: chloroform) in order to obtain finally 570 mg. of benzyl 6'-(2″-benzyloxycarbonylamino-2″-phenylacetamido)-spiro[cyclopentane-1,2'-penam]-3'-carboxylate. M.P. 58°-60° C. Yield: 95%.

Analysis (in % by weight) for $C_{33}H_{33}N_3O_6S$ (M.W. 596): Calculated: C, 65.89; H, 5.49; N, 6.98. Found: C, 67.70; H, 5.80; N, 7.30.

| Infra-red spectrum in KBr (in cm⁻¹): | |
|---|---|
| 3305 | (NH) |
| 1778 | (CO beta-lactam) |
| 1734 | (CO ester) |
| 1669 | (CO amide) |
| 745, 694 | (monosubstituted phenyl rings) |

-continued

| NMR spectrum (CDCl₃—TMS) | | |
| --- | --- | --- |
| 1.7 ppm | multiplet | 8H (cyclopentyl) |
| 4.6 ppm | doublet | 1H (H₃·) |
| 5.11 ppm | singlet | 2H (CH₂ of the benzyl ester) |
| 5.20 ppm | singlet | 2H (CH₂ of the benzyloxy-carbonyl group) |
| 5.45 ppm | quartet | (J=4 cycles per second) 2H (H₅· and H₆·) |
| 6.10 ppm | doublet | (J=6 cycles per second) 1H (H₂·) |
| 6.50 ppm | multiplet | 2H (2 × —NH—) |
| 7.34 ppm | multiplet | 5H (phenyl) |
| 7.38 ppm | singlet | 10H (phenyl of the benzyl ester and of the benzyloxycarbonyl group) |

(b) 6'-(2''-amino-2''-phenylacetamido)-spiro[cyclopentane-1,2'-penam]-3'-carboxylic acid.

10 ml. of water and 0.6 g. of palladium/carbon catalyst (10% Pd) are added to a solution of 450 mg. (0.000748 mole) of benzyl 6'-(2''-benzyloxycarbonylamino-2''-phenylacetamido)-spiro[cyclopentane-1,2'-penam]-3'-carboxylate in 10 ml. of ethyl acetate. Hydrogenolysis is carried out at ambient temperature at a pressure of 2 atmospheres. The reaction mixture is then filtered over "Hyflo-cel", washed with about 100 ml. of water and lyophilized. 90 mg. (0.00024 mole) of 6'-(2''-amino-2''-phenylacetamido)-spiro[cyclopentane-1,2'-penam]-3'-carboxylic acid are thus obtained. M.P. 223°–226° C. (decomposition). Yield: 32%.

| Infra-red spectrum in KBr (in cm⁻¹): | |
| --- | --- |
| 3400 | (NH₂, COOH) |
| 1760 | (CO beta-lactam) |
| 1672 | (CO amide) |
| 1590 | (carboxylate) |
| 720 and 690 | (monosubstituted phenyl) |
| NMR spectrum (DMSO—TMS): | |
| 1.65 ppm | multiplet | 8H (cyclopentyl) |
| 4.25 ppm | singlet | 1H (H₃·) |
| 4.90 ppm | singlet | 1H (H₂·) |
| 5.43 ppm | multiplet | 2H (H₅· and H₆·) |
| 7.45 ppm | singlet | 5H (phenyl) |

We claim:

1. A member selected from the group consisting of a 6'-amino-spiro[cycloalkane-1,2'-penam]-3'-carboxylic acid compound of the formula

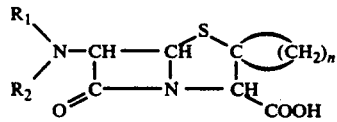

wherein
n is a whole number of from 3 to 6,
R₁ is a hydrogen atom, and
R₂ is a radical selected from the group consisting of 2-phenylacetyl, 2,6-dimethoxybenzoyl, 2-amino-2-phenylacetyl, 5-methyl-3-phenyl-4-isoxazolecarbonyl and 2-carboxy-2-phenylacetyl, or
R₁ and R₂ together represent (hexahydro-1H-azepin-1-yl)methylene, and
a therapeutically acceptable non-toxic salt thereof.

2. A compound as claimed in claim 1, wherein R₂ is a radical selected from the group consisting of 2-phenylacetyl, 2,6-dimethoxybenzoyl, 2-amino-2-phenylacetyl, 5-methyl-3-phenyl-4-isoxazolecarbonyl and 2-carboxy-2-phenylacetyl.

3. A compound as claimed in claim 1, wherein R₁ and R₂ together represent (hexahydro-1H-azepin-1-yl)methylene.

4. A compound as claimed in claim 1, namely potassium 6'-(2''-phenylacetamido)-spiro[cyclohexane-1,2'-penam]-3'-carboxylate.

5. A compound as claimed in claim 1, namely potassium 6'-(2''-phenylacetamido)-spiro[cyclopentane-1,2'-penam]-3'-carboxylate.

6. A compound as claimed in claim 1, namely potassium 6'-(2''-phenylacetamido)-spiro[cyclobutane-1,2'-penam]-3'-carboxylate.

7. A compound as claimed in claim 1, namely sodium 6'-(2'',6''-dimethoxybenzamido)-spiro[cyclohexane-1,2'-penam]-3'-carboxylate.

8. A compound as claimed in claim 1, namely sodium 6'-(2'',6''-dimethoxybenzamido)-spiro[cyclopentane-1,2'-penam]-3'-carboxylate.

9. A compound as claimed in claim 1, namely sodium 6'-(5''-methyl-3''-phenyl-4''-isoxazolecarboxamido)-spiro[cyclohexane-1,2'-penam]-3'-carboxylate.

10. A compound as claimed in claim 1, namely 6'-(2''-amino-2''-phenylacetamido)-spiro[cyclohexane-1,2'-penam]-3'-carboxylic acid.

11. A compound as claimed in claim 1, namely sodium 6'-(2''-amino-2''-phenylacetamido)-spiro[cyclohexane-1,2'-penam]-3'-carboxylate.

12. A compound as claimed in claim 1, namely 6'-(2''-amino-2''-phenylacetamido)-spiro[cyclopentane-1,2'-penam]-3'-carboxylic acid.

13. A composition for the treatment of an infectious disease caused by Gram-positive or Gram-negative bacteria, which comprises a pharmaceutical carrier and a therapeutically effective amount of a member selected from the group consisting of a 6'-amino-spiro[cycloalkane-1,2'-penam]-3'-carboxylic acid compound of the formula

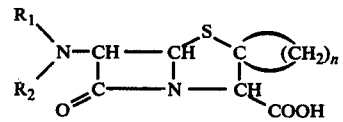

wherein n is a whole number of 3 to 6,
R₁ is a hydrogen atom and R₂ is a radical selected from the group consisting of 2-phenylacetyl, 2,6-dimethoxybenzoyl, 2-amino-2-phenylacetyl, 5-methyl-3-phenyl-4-isoxazolecarbonyl and 2-carboxy-2-phenylacetyl, or R₁ and R₂ together represent (hexahydro-1H-azepin-1-yl)methylene,
and a therapeutically acceptable non-toxic salt thereof.

14. A method for the treatment of an infectious disease caused by Gram-positive or Gram-negative bacteria, which comprises administering to a patient suffering from said disease an amount of from 0.1 to 8 g per day of a member selected from the group consisting of a 6'-amino-spiro[cycloalkane-1,2'-penam]-3'-carboxylic acid compond of the formula

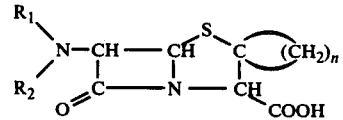

wherein n is a whole number of from 3 to 6, $R_1$ is a hydrogen atom and $R_2$ is a radical selected from the group consisting of 2-phenylacetyl, 2,6-dimethoxybenzoyl, 2-amino-2-phenylacetyl, 5-methyl-3-phenyl-4-isoxazolecarbonyl and 2-carboxy-2-phenylacetyl, or $R_1$ and $R_2$ together represent (hexahydro-1H-azepin-1-yl)methylene, and a therapeutically acceptable non-toxic salt thereof.

15. A compound as claimed in claim 1, wherein $R_2$ is 2,6-dimethoxybenzoyl or 5-methyl-3-phenyl-4-isoxazolecarbonyl.

* * * * *